(12) United States Patent
Wada et al.

(10) Patent No.: US 6,338,729 B1
(45) Date of Patent: Jan. 15, 2002

(54) URINE ABSORBING PAD

(75) Inventors: Ichiro Wada; Noriyuki Kurita; Kouzou Abe, all of Kagawa (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 09/418,412

(22) Filed: Oct. 14, 1999

(30) Foreign Application Priority Data

Oct. 30, 1998 (JP) .......................................... 10-309861

(51) Int. Cl.[7] .................................................. A61F 13/15
(52) U.S. Cl. .............. 604/385.09; 604/349; 604/385.01
(58) Field of Search .................................. 604/378, 369, 604/370, 372, 374, 380, 383, 385.01, 349, 358, 367, 385.03, 385.09, 385.101, 385.201, 385.24

(56) References Cited

U.S. PATENT DOCUMENTS

| | | | | |
|---|---|---|---|---|
| 2,445,220 A | * | 7/1948 | Isaacson | 128/295 |
| 3,366,116 A | * | 1/1968 | Huck | 128/295 |
| 3,368,561 A | * | 2/1968 | Ericson et al. | 128/275 |
| 4,668,229 A | * | 5/1987 | Fago et al. | 604/327 |
| 4,772,280 A | * | 9/1988 | Rooyakkers | 604/349 |
| 4,886,509 A | | 12/1989 | Mattsson | |
| 4,963,137 A | | 10/1990 | Heyden | |
| 5,342,332 A | | 8/1994 | Wheeler | |
| 5,439,458 A | * | 8/1995 | Noel et al. | 604/378 |
| 5,827,250 A | * | 10/1998 | Fjioka et al. | 604/349 |

FOREIGN PATENT DOCUMENTS

| | | |
|---|---|---|
| EP | 0 228 353 | 7/1987 |
| FR | 2 701 389 A1 | 8/1994 |
| JP | S63-160815 | 10/1988 |
| JP | 404096748 A * | 3/1992 |
| JP | H4-44913 | 4/1992 |
| JP | H6-26828 | 4/1994 |
| WO | 81/03609 | 12/1981 |

* cited by examiner

*Primary Examiner*—John G. Weiss
*Assistant Examiner*—Jackie Stephens
(74) *Attorney, Agent, or Firm*—Milbank, Tweed, Hadley & McCloy LLP

(57) ABSTRACT

A urine absorbing pad comprising a laminate including: a liquid penneable internal surface sheet; a liquid impermeable external surface sheet; and an absorbent core sandwiched between the internal and external surface sheets. The laminate forming a bag body having an opening, at which the internal surface sheet is directed inward, the opening being positioned closer to an upper end of the bag body than to a lower end of the bag body. The upper end and the lower end are extended substantially at a right angle with resect to each other. The opening is formed into a slit shape having a longitudinal direction from the upper end toward the lower and.

16 Claims, 9 Drawing Sheets

URINE ABSORBING PAD

FIELD OF THE INVENTION

The present invention relates to a urine absorbing pad to be used for the incontinence of urine and, more particularly, it relates to a urine absorbing pad which is in a bag shape having an opening.

BACKGROUND OF THE INVENTION

In general, a urine absorbing pad for males to be employed for the incontinence of urine is constructed of a laminate which is composed of a liquid permeable internal surface sheet, a liquid impermeable external surface sheet and an absorbent core sandwiched between the internal and external surface sheets. The absorbent core is made of absorbent fibers such as pulp or a mixture of absorbent fibers and super absorbent polymer (SAP).

The urine absorbing pad is constructed such that the laminate is folded in two and bonded along its side edge portions into a bag shape having an opening for insertion of the penis at its upper end. Alternatively, the urine absorbing pad is constructed such that the laminate, which is commercially available in a flat shape, is folded into a cone shape upon use to wrap the penis.

However, it is laborious to wear the prior art urine absorbing pad which is constructed by forming the flat laminate into a cone shape upon use. Further, the cone shape is so unstable as to allow urine to leak from the clearance in the folded laminate. Especially, when the wearer changes his position while turning on the bed, the pad is liable to be deformed to cause that leakage.

On the other hand, it is easy to wear the prior art urine absorbing pad which is constructed by forming the laminate into a bag shape in its production process. However, in such a bag-shaped urine absorbing pad, when the penis is inserted into the opening, the positional relation between the opening and the penis is unstable. This may allow the penis to come out of the opening when the wearer changes his position. Further, the urine easily leaks to the outside from the clearance between the opening and the penis. Moreover, since the bag-shaped urine absorbing pad is formed by folding the laminate in two, it is difficult to enlarge the volume of the pad in the groin. As a result, the urine absorbing capacity is not sufficient.

SUMMARY OF THE INVENTION

The present invention solves the above-specified problems in the prior art and has an object to provide a urine absorbing pad which can be stably worn in the groin.

Another object of the invention is to provide a urine absorbing pad which can absorb more urine.

Still another object of the invention is to provide a urine absorbing pad which can clamp the penis reliably, while reducing the discomfort to the penis.

The present invention provides a urine absorbing pad comprising a laminate including: a liquid permeable internal surface sheet; a liquid impermeable external surface sheet; and an absorbent core sandwiched between the internal and external surface sheets, the laminate forming a bag body having an opening, at which the internal surface sheet is directed inward, the opening being positioned closer to an upper end of the bag body than to a lower end of the bag body, wherein the upper end and the lower end are extended substantially at a right angle with respect to each other.

With the upper end and the lower end substantially at a right angle, the bag body can conform to the shape of the groin, so that the urine absorbing pad can be stably worn in the groin. In addition, the urine absorbing capacity is effectively enhanced.

In carrying out the invention in one preferred mode, the laminate is substantially symmetric, when in a developed state, with respect to a center line and has an upper edge portion and a lower edge portion opposed to each other, and side edge portions substantially symmetric with respect to the center line, wherein the bag body is formed such that two side portions of the upper edge portion are folded along folding lines, which are substantially symmetric with respect to the center line, toward a central portion of the upper edge portion thereby to form the upper end; the lower edge portion is folded along the center line into two thereby to form the lower end; and the side edge portions confront each other.

In carrying out the invention in another preferred mode, the laminate is substantially symmetric, when in an extended state, with respect to a center line and has an upper edge portion and a lower edge portion opposed to each other, and side edge portions substantially symmetric with respect to the center line, wherein the bag body is formed such that the upper edge portion and the lower edge portion are individually folded along the center line into two so that the center line forms the lower end, and the side edge portions are individually folded into two to form the upper end.

Moreover, the present invention provides a urine absorbing pad comprising a laminate including a liquid permeable internal surface sheet; a liquid impermeable external surface sheet; and an absorbent core sandwiched between the internal and external surface sheets, the laminate forming a bag body having an opening, at which the internal surface sheet is directed inward, the opening being positioned closer to an upper end of the bag body than to a lower end of the bag body, wherein the opening is formed into a slit shape having a longitudinal direction from the upper end toward the lower end.

With this slit-shaped opening having its longitudinal direction extended from the upper end toward the lower end, the penis is effectively prevented from coming out of the urine absorbing pad, so that the urine absorbing pad can be stably worn in the groin. In addition, because this slit-shaped opening does not press the urethra too strong, the discomfort to the penis can be prevented.

DETAILED DESCRIPTION OF THE INVENTION

The present invention will be described hereinafter with reference to the accompanying drawings.

Figure 1:
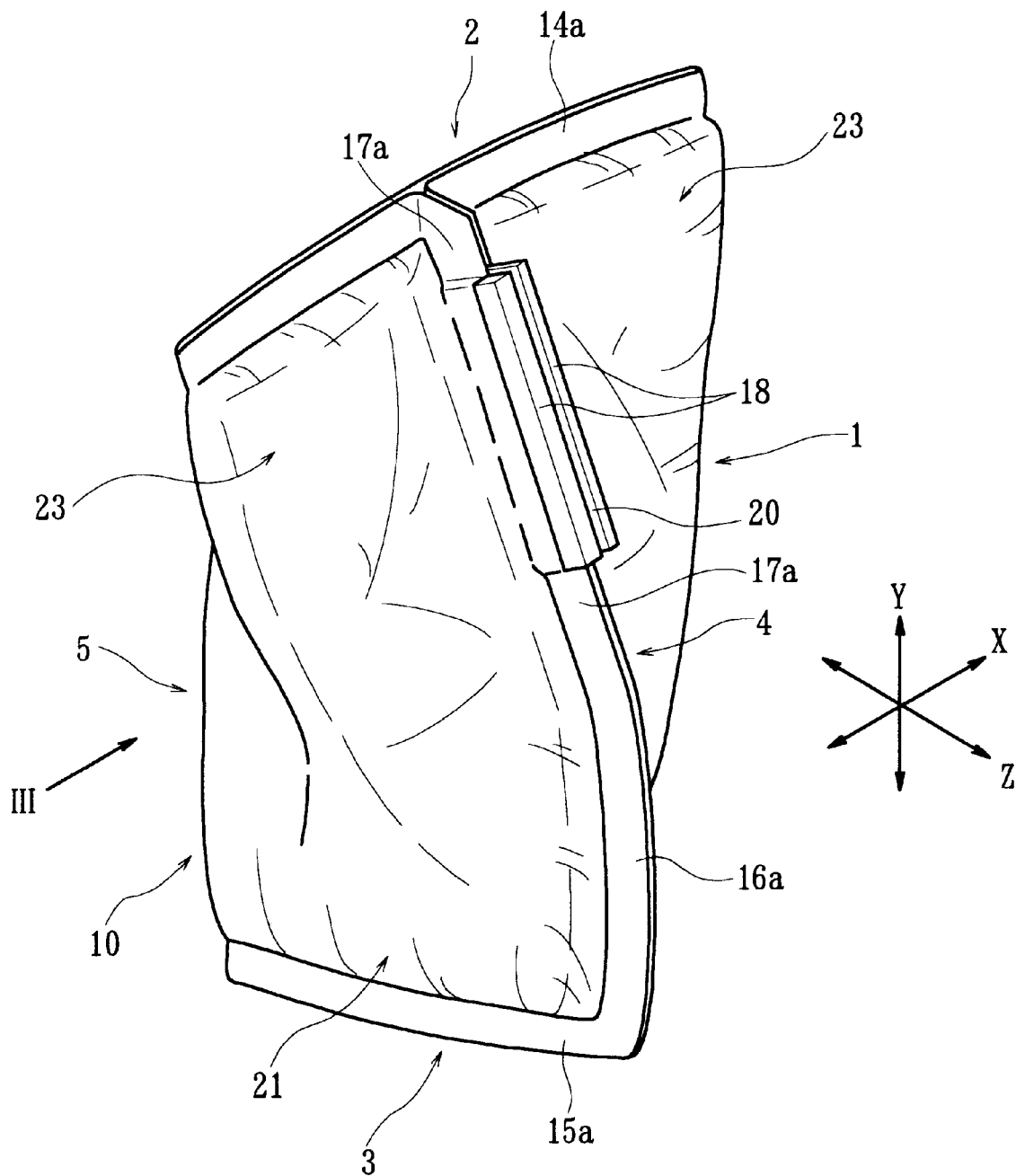
FIG. 1 is a perspective view showing a urine absorbing pad as an embodiment of the invention.
Figure 2:
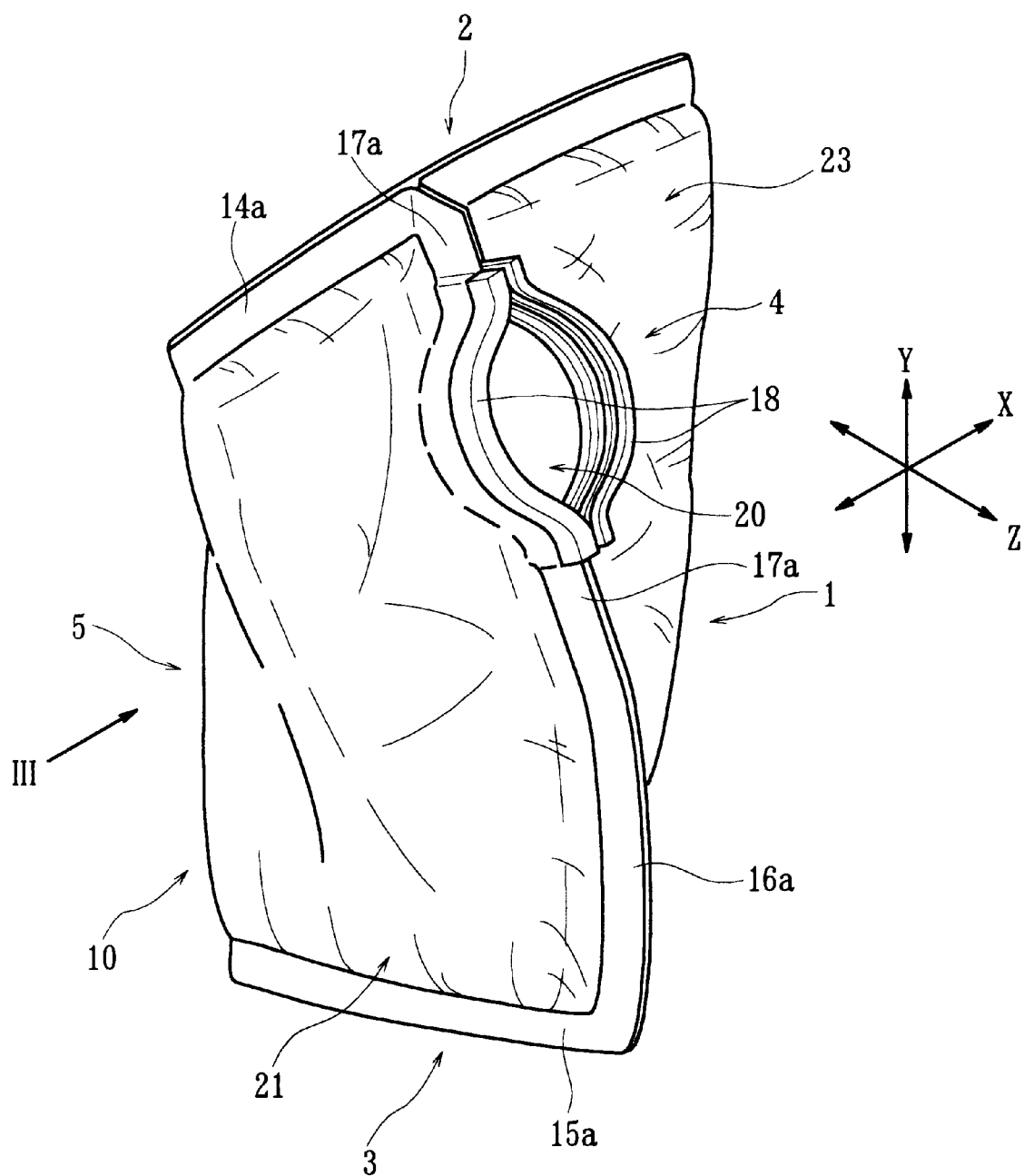
FIG. 2 is a perspective view showing the state in which an opening of the urine absorbing pad of FIG. 1 is widened.
Figure 3:
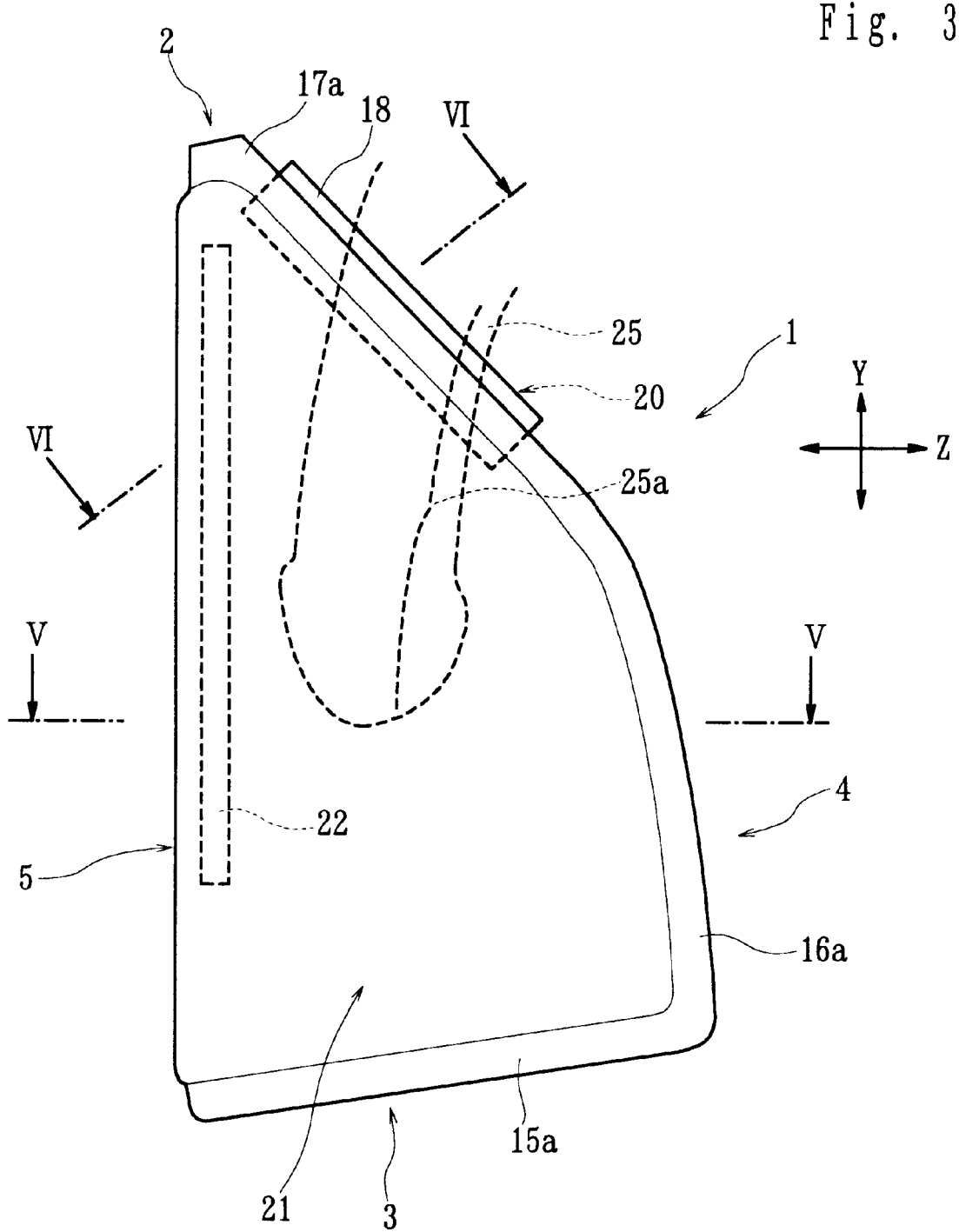
FIG. 3 is a side view showing the state of the urine absorbing pad of FIG. 1 in use, as taken from a side III.
Figure 4:
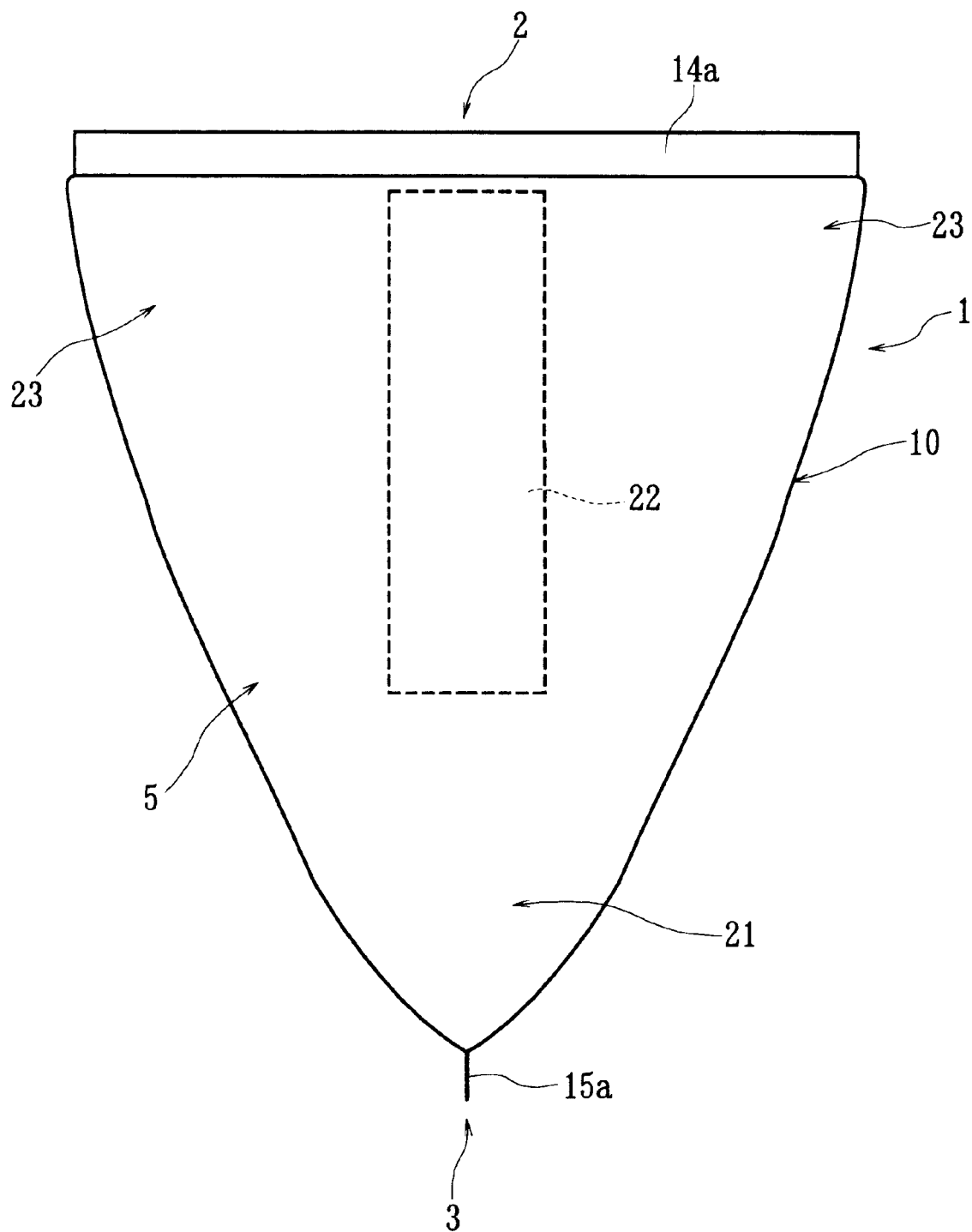
FIG. 4 is a back view of the urine absorbing pad of FIG. 1.
Figure 5:
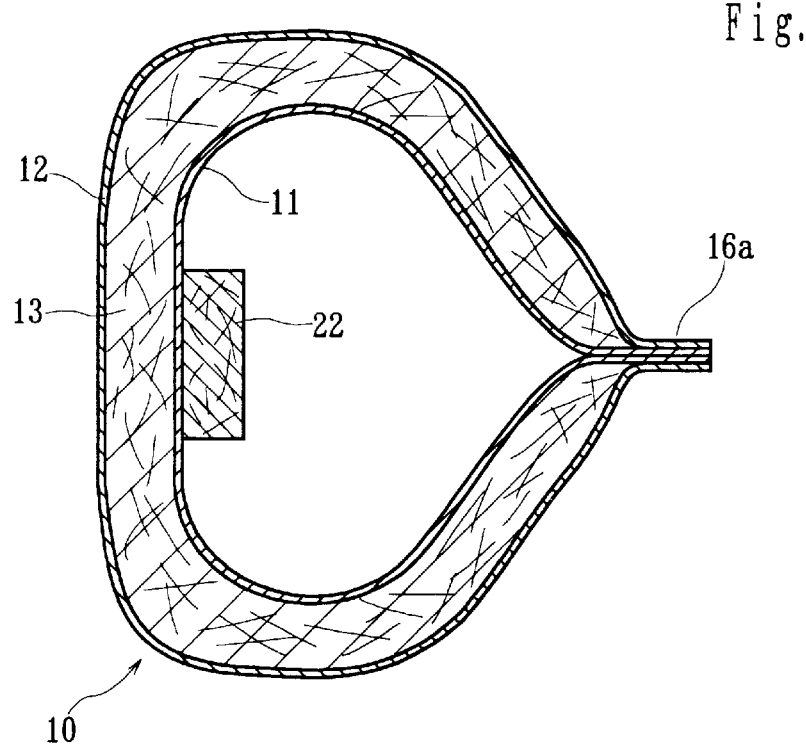
FIG. 5 is a sectional view taken along line V—V of FIG. 3.
Figure 6:
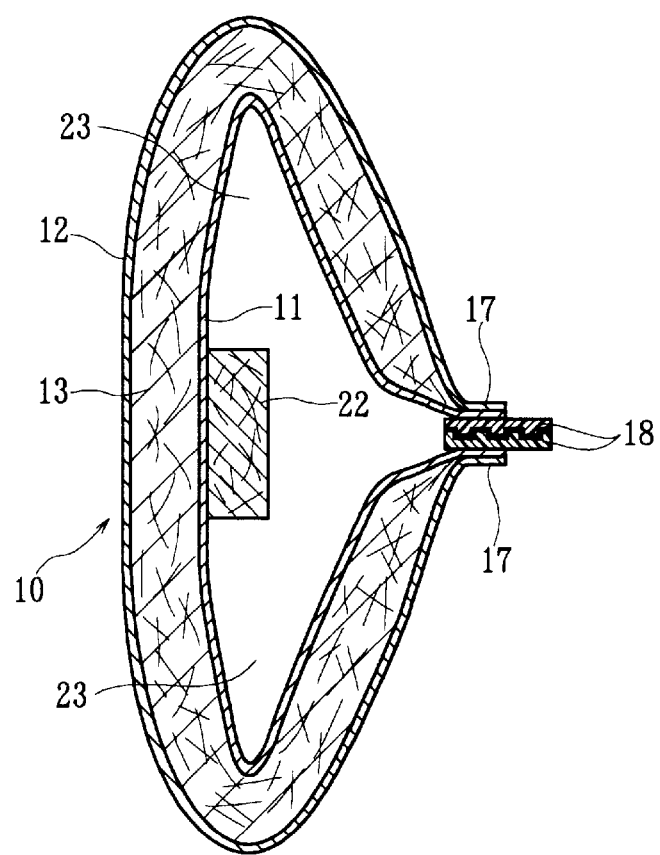
FIG. 6 is a sectional view taken along line VI—VI of FIG. 3.
Figure 7:
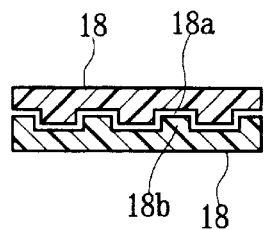
FIG. 7 is an enlarged view of a portion of an elastic member of FIG. 6.

FIG. 1 is a perspective view showing a urine absorbing pad as an embodiment of the invention, as taken from a wearing side; FIG. 2 is a perspective view showing the state in which an opening of the urine absorbing pad of FIG. 1 is widened; FIG. 3 is a side view, as taken from side III of FIG. 1; FIG. 4 is a back view, as taken from a side opposite to the wearing side of FIG. 1; FIG. 5 is a sectional view taken along line V—V of FIG. 3; FIG. 6 is a sectional view taken along line VI—VI of FIG. 3; FIG. 7 is a partially enlarged view of FIG. 6; and FIG. 8 is a perspective view showing the developed state of the urine absorbing pad.

The embodiment, as shown in FIGS. 1 to 7, is a urine absorbing pad for a male adult. A bag body 1 of this urine absorbing pad has an upper end 2 and a lower end 3. In this bag body 1, a direction Y, from the upper end 2 to the lower end 3, is made longitudinal; a direction X perpendicular to the direction Y is made transverse; and a direction Z is made thick. In this direction Z (in thick direction), a side appearing in FIGS. 1 and 2 is designated a wearing side 4, which is to be applied to the wearer, and an opposite side appearing in FIG. 4 is designated a back side 5.

The bag body 1 is constructed of a laminate 10. This laminate 10 is composed of a liquid-permeable internal surface sheet 11, a liquid-impermeable external surface sheet 12 and an absorbent core (or a liquid absorbing member) 13 sandwiched between the sheets 11 and 12, as shown in sectional views of FIGS. 5 and 6. The liquid-permeable internal surface sheet 11 is made of, for example, point bonded, air-through, spun-bonded or spun-laced non-woven fabric of hydrophilized hydrophobic fibers or hydrophilic fibers. The "hydrophilized hydrophobic fibers" as used herein means hydrophobic fibers subjected to hydrophilic treatment. In this hydrophilic treatment, a hydrophobic fiber is made hydrophilic by treating it with a surfactant; by chemically binding a chemical substance such as a monomer or a polymer having a hydrophilic group thereto; by subjecting it to plasma processing; by kneading it with a chemical substance having a hydrophilic group; or by treating its surface to have a profiled section. The liquid-impermeable external surface sheet 12 is made of a resin sheet such as of olefin, for example. The external surface sheet 12 is preferably prepared by laying point-bonded non-woven fabric on the outer surface of a transparent or semitransparent polyethylene film. If this external surface sheet 12 is employed, the discoloration of the absorbent core 13, which will be caused by absorbing much urine, can be visually confirmed from the outside. Moreover, since the outer surface of the external surface sheet 12 is made of the non-woven fabric, it can prevent the urine absorbing pad from slipping on a diaper and moving out of position, when the urine absorbing pad is used on the inner side of the diaper. Alternatively, an adhesive layer for stopping the slippage from the diaper may be provided on the surface of the back side 5 shown in FIG. 4. The absorbent core 13 is made of crushed pulp or a mixture of crushed pulp and super absorbent polymer (SAP) which is enveloped with an absorbent sheet such as tissue paper. The SAP can be made of polyacrylic acid, sodium polyacrylate, polyacrylamide, polyacrylonitrile, polyvinyl alcohol, an additional polymer of maleic anhydride, a polyether, a condensed polymer, a polysaccharide such as starch or cellulose, a protein such as collagen, or the like. Examples of the SAPs include: a cross-linked compound of sodium polyacrylate, a graft copolymer of starch having sodium polyacrylate or a graft copolymer of cellulose having polyacrylonitrile chains. Alternatively, the absorbent core 13 may be made of SAP and non-woven fabrics of hydrophilic fibers such that the non-woven fabrics are partially bonded to each other having the SAP dispersed therebetween.

Figure 8:
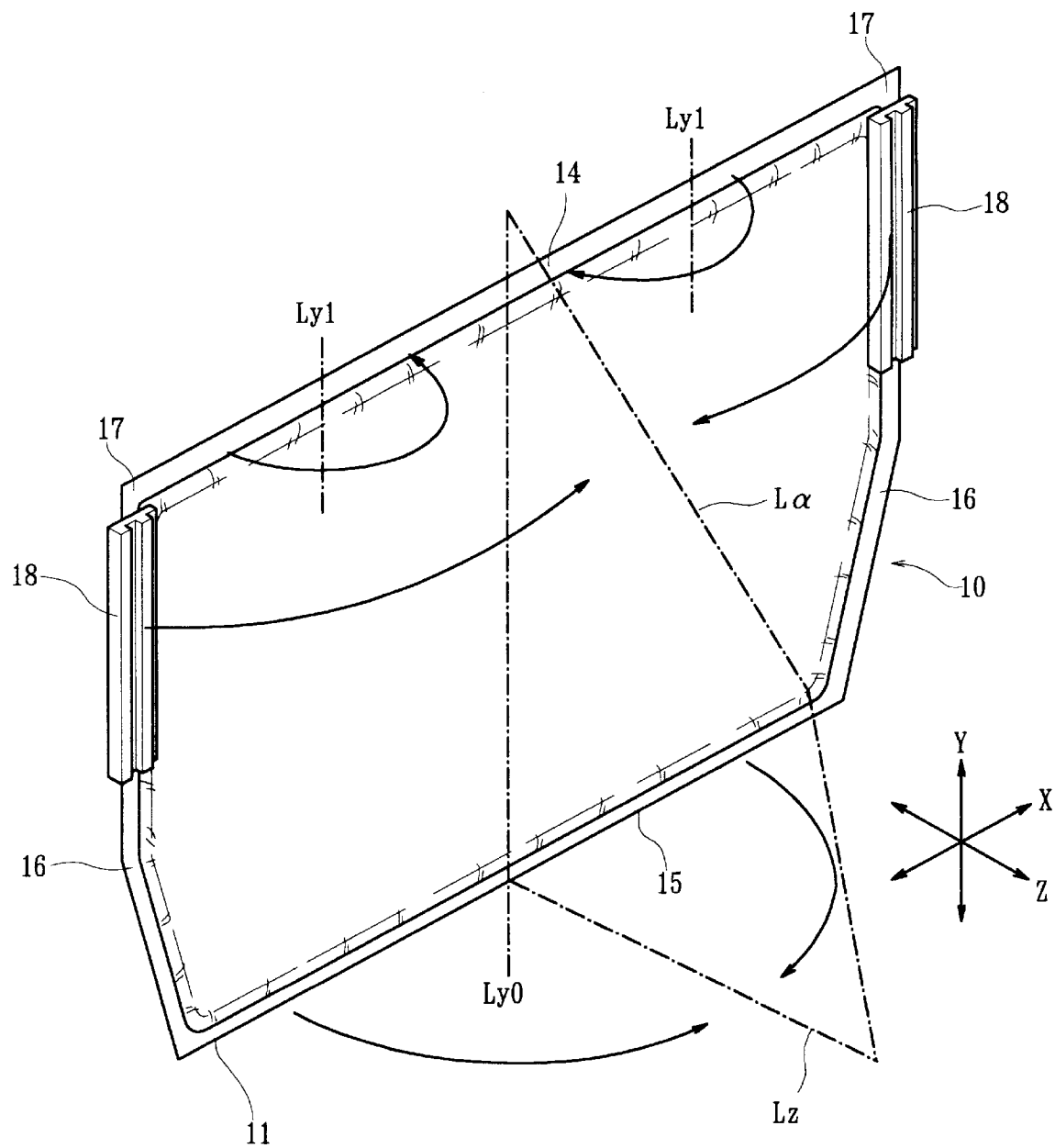
FIG. 8 is a perspective view showing the developed state of the urine absorbing pad of FIG. 1.

FIG. 8 shows the developed state of the laminate 10 constructing the bag body 1. The laminate 10 in the developed state takes a generally flat sheet shape, in which the absorbent core 13 is absent from individual edge portions 14, 15, 16 and 17. That is, the internal surface sheet 11 and the external surface sheet 12 are extended to the outside of the absorbent core 13, at the edge portions 14, 15, 16 and 17, and are bonded to each other by an adhering treatment using a hot-melt type adhesive, by a heat-sealing treatment or by a composite treatment using an adhesive and a heat-seal. Alternatively, the absorbent core 13 may be present at the edge portions 14, 15, 16 and 17. In the developed state shown in FIG. 8, the edge portion 14 at the upper end and the edge portion 15 at the lower end are parallel to each other; the edge portions 17 and 17 at the opposite transverse sides and adjacent to the upper end are parallel to each other; and the edge portions 16 and 16 at the opposite transverse sides and adjacent to the lower end are sloped to approach each other on the lower end side. This laminate 10 in the developed state is substantially symmetric with respect to a center line Ly0. With the bag body 1 being formed, the edge portions 17 and 17 form an opening 20 with their confronting faces. To the edge portions 17 and 17, further, there are respectively bonded and fixed elastic members 18 and 18 which construct fastening means (or holding means) for the penis. These elastic members 18 and 18 are preferred to give a soft contacting feel to the skin but not to have a high elastic restoring force. Therefore, the elastic members 18 and 18 may be made of hard foamed urethane, for example. Alternatively, the elastic members 18 and 18 can also be formed of plastic sheets or card boards impregnated with a resin.

The laminate 10, as shown in FIG. 8, is folded at its lower end edge portion 15 into a valley along the longitudinal center line Ly0, and the righthand and lefthand halves of the edge portion 15 are confronted and bonded to each other on virtual line Lz extending in the thick direction (or the direction Z). On the other hand, the upper end edge portion 14 is folded along folding lines Ly1 and Ly1 which are set at positions spaced by about one quarter of the transverse size of the edge portion 14 from its transverse ends, and the righthand and lefthand folded portions of the edge portion 14 are confronted and bonded to the central portion of the edge portion 14. Consequently, the edge portions 16 and 16 are confronted and bonded to each other on a virtual line Lα extending obliquely in the longitudinal direction. On the other hand, the edge portions 17 and 17 carrying the elastic members 18 and 18 are also confronted to each other on the virtual line Lα, but are bonded to each other exclusively at their upper and lower portions excepting the elastic members 18 and 18. The bonding operations of those individual edge portions are effected by an adhering treatment using a hot-melt type adhesive, by a heat-sealing treatment or by a composite treatment using an adhesive and a heat-seal.

As a result, there is formed the bag body 1, as shown in FIGS. 1 and 2. In this bag body 1, the edge portion 14 is folded and closed to form a joint portion 14a, thereby providing the upper end 2, and the edge portion 15 is folded and closed to form a joint portion 15a, thereby providing the lower end 3. The joint portion 14a (i.e., the upper end 2) extends in the transverse direction (or in the direction X) whereas the joint portion 15a (ie., the lower end 3) extends in the thick direction (or in the direction Z). In short, the joint portions 14a and 15a extend substantially at a right angle with respect to each other, so that the bag body 1 takes the so-called "tetra pack" type stereoscopic shape. On the wearing side 4 of the bag body 1, on the other hand, there is formed a joint portion 16a which is prepared by bonding the edge portions 16 to each other, and there is formed joint portions 17a which are prepared by partially bonding the edge portions 17 to each other. At a position close to the upper end 2, preferably at a position substantially merging into the upper end 2, there is formed the opening 20 in which the elastic members 18 and 18 are opposed to each other. This opening 20 extends longitudinally (or in a slit shape) between the upper end 2 and the lower end 3. In this bag body 1, there is formed a urine absorbing space 21 which has a relatively large capacity, at a portion closer to the lower end 3 than the portion having the opening 20. Here, as shown in FIG. 4, the back side 5, as opposed to the wearing side 4, takes a generally triangular shape having no joint portion.

Moreover, as shown in FIGS. 3, 4, 5 and 6, a urine guide layer 22 is provided on the surface of the internal surface sheet 11 of the laminate 10 forming the back side 5. This urine guide layer 22 is made of a fiber layer of low density such as air through non-woven fabric of hydrophilized hydrophobic fibers or hydrophilic fibers. The urine guide layer 22 is longitudinally extended from a position confronting the opening 20 to the urine absorbing space 21.

When the urine absorbing pad thus constructed is to be used, its wearing side 4 is directed toward the wearer's abdomen, and two longitudinal ends of the elastic members 18 and 18 are pinched with fingers to apply a longitudinal compression. Then, the individual elastic members 18 and 18 are buckled and deformed away from each other, as shown in FIG. 2, so that the opening 20 is transversely widened. The penis 25 is inserted through the widened opening 20 into the bag body 1, as shown in FIG. 3, and the elastic members 18 and 18 are released from the compression. Then, the elastic members 18 and 18 elastically restore to clamp and hold the root portion of the penis 25 softly from the transverse sides.

As shown in FIG. 3, the penis 25 has a urethra 25a located on the lower side thereof and generally at the center in the transverse direction. Therefore, if the penis 25 is pressed vertically (or in the direction Z), the urethra 25a is pressed strongly so that the wearer feels a discomfort when he passes urine and the speed of passing urine drops. However, in this urine absorbing pad, since the penis 25 is clamped from the transverse sides by the elastic members 18 and 18, the urine absorbing pad does not press the urethra 25a such that there is neither discomfort nor an attenuation of the speed of passing urine.

The elastic members 18 and 18 are made of a foamed material to clamp the penis 25 softly by the restoration of the buckling deformation so that they apply a considerably light pressure to the penis 25. If grooves 18a and ridges 18b are formed at the opposed faces of the elastic members 18 and 18, as shown in FIG. 7, they can come into abutment against the penis 25 to suppress the slippage frictionally between the penis 25 and the elastic members 18 and 18. As a result, the penis 25 hardly comes out of the opening 20.

Moreover, since the opening 20 is longitudinally elongated in the side face between the upper end 2 and the lower end 3, the penis 25 hardly comes out transversely with respect to the opening 20 once it is inserted from the opening 20 into the bag body 1. As a result, the penis 25 hardly comes out of the opening 20, even when the wearer's position changes to move the pad in the diaper, for example.

The bag body 1 constructing this urine absorbing pad has a sufficiently smaller size in the thick direction (or the direction Z) at its portion having the opening 20 than that at its lower end 3. In other words, the bag body 1 is so flattened at the portion having the opening 20 as to extend in the transverse direction (or in the direction X) and at the lower end 3 as to extend in the thick direction (or in the direction Z). Therefore, when the bag body 1 is put on the abdomen, the flattened portion having the opening 20 will have less bulge forward of the body (or in the direction Z). As a result, when the urine absorbing pad thus worn is covered with the diaper, the forward bulge of the diaper at the abdomen is so small that the urine absorbing pad is stably pushed on the abdomen by the diaper. Moreover, since the bag body 1 is held at its lower end 3 in the groin, the urine absorbing pad hardly goes out of position in the transverse directions even the wearer changes his lying position. Thus, the urine absorbing pad is so stabilized in the diaper as to hardly go out of position even with a change in position of the wearer, so that the penis 25 hardly comes out of the opening 20. Still further, because the back side 5 to face the diaper has no joint portion, the urine absorbing pad comes into close contact with the diaper, so that the urine absorbing pad is stabilized in the diaper.

In the case of incontinence or passing of urine in the state shown in FIG. 3, the urine is absorbed by the absorbent core 13 in the urine absorbing space 21 under the opening 20. In this urine absorbing space 21, the bag body 1 can extend in the thick direction (or in the direction Z) to retain a relatively wide urine absorbing area by the laminate 10 thereby to remarkably enlarge the capacity for absorbing the urine.

At the portion having the opening 20, on the other hand, the bag body 1 has a transverse extension to provide spare spaces 23 (as shown in FIG. 6) which are formed of the laminate 10 on the transverse sides of the opening 20. Therefore, when the wearer of the urine absorbing pad takes a lateral position while turning in his bed (or when the wearer is lying on his side), the absorbent core 13 in the spare spaces 23 can absorb the urine which will flow transversely in the bag body 1. This prevents urine from leaking from the opening 20 to the outside when the wearer passes urine in his lateral position.

Moreover, with the urine guide layer 22 extending from the portion confronting the opening 20 into the urine absorbing space 21, the urine can be guided into the urine absorbing space 21 having a high urine absorbing capacity. Therefore, at the time of urination in the lateral position of the wearer, even much urine can be absorbed by exploiting the absorbing ability of the urine absorbing space 21 so that the leakage from the opening 20 can also be prevented in this case.

Figure 9:
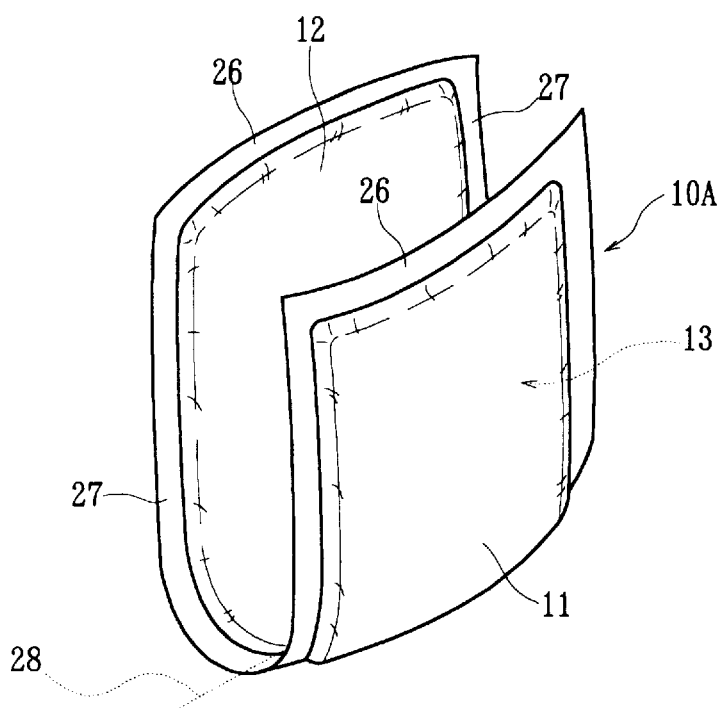
FIG. 9(A) is a perspective view showing a laminate in the process of being formed into a urine absorbing pad as another embodiment of the invention.
FIG. 9(B) is a perspective view showing the urine absorbing pad formed from the laminate of FIG. 9(A)
Figure 9:
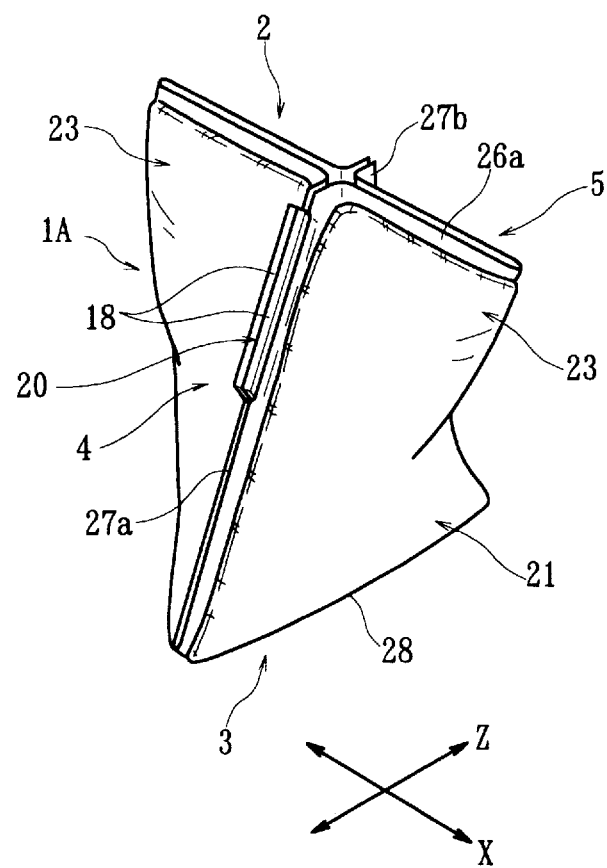

FIG. 9(B) is a perspective view showing a urine absorbing pad of another embodiment of the invention, and FIG. 9(A)

is a perspective view showing a laminate before forming the urine absorbing pad in FIG. 9(B). Here, the detailed description of the portions having the same constructions as those of the first embodiment will be omitted by designating them by the common reference numerals. In this embodiment, as shown in FIG. 9(A), there is used a rectangular laminate 10A which includes the internal surface sheet 11, the external surface sheet 12 and the absorbent core 13 sandwiched between the sheets 11 and 12. The internal surface sheet 11 and the external surface sheet 12 are bonded to each other at shorter edge portions (or side edge portions) 26 and 26 and at longer edge portions (or upper and lower edge portions) 27 and 27 of the laminate 10A, by using an adhesive or the like. Here, this rectangular laminate 10A is substantially symmetric with respect to a folding portion 28.

First, as shown in FIG. 9(A), the laminate 10A is folded into the shape of the letter "U" along the folding portion 28. Then, as shown in FIG. 9(B), the longer edge portions 27 are individually bonded to form joint portions 27a and 27b extending longitudinally. Thereafter, the upper portion, which is composed of the shorter edge portions 26 and 26 and extends in the direction Z, is flattened in the transverse direction (or in the direction X) and bonded to form a joint portion 26a.

As a result, there is formed a bag body 1A in which the joint portion 26a (i.e., the upper end 2) extends in the transverse direction (or in the direction X) whereas the folding portion 28 (ie., the lower end 3) extends in the thick direction (or in the direction Z). In this bag body 1A, the joint portion 27a appears on the wearing side 4. Here, a portion of the joint portion 27a is not bonded while being provided with the elastic members 18 and 18, thereby forming the opening 20 at a position close to the upper end 2. On the other hand, the joint portion 27b appears on the back side 4. The joint portion 27b is closed along its entire length.

The urine absorbing pad shown in FIG. 9(B) also has the urine absorbing space 21 formed below the opening 20 and extended in the thick direction, and the spare spaces 23 and 23 formed on the transverse sides of the opening 20, so that it can also exhibit a urine absorbing function similar to that of the urine absorbing pad shown in FIGS. 1 and 2.

In the urine absorbing pad shown in FIG. 9(B), moreover, the laminate 10A is folded at the folding portion 28 to form the lower end 3 so that the absorbent core 13 exists at the lower end 3. Therefore, this enhances the urine absorbing ability at the lower end 3.

Here in the foregoing individual embodiments, the elastic members 18 and 18 are provided at the opening 20 but could be omitted to form the slit-shaped opening 20 between the edge portions of the laminate.

Figure 10:
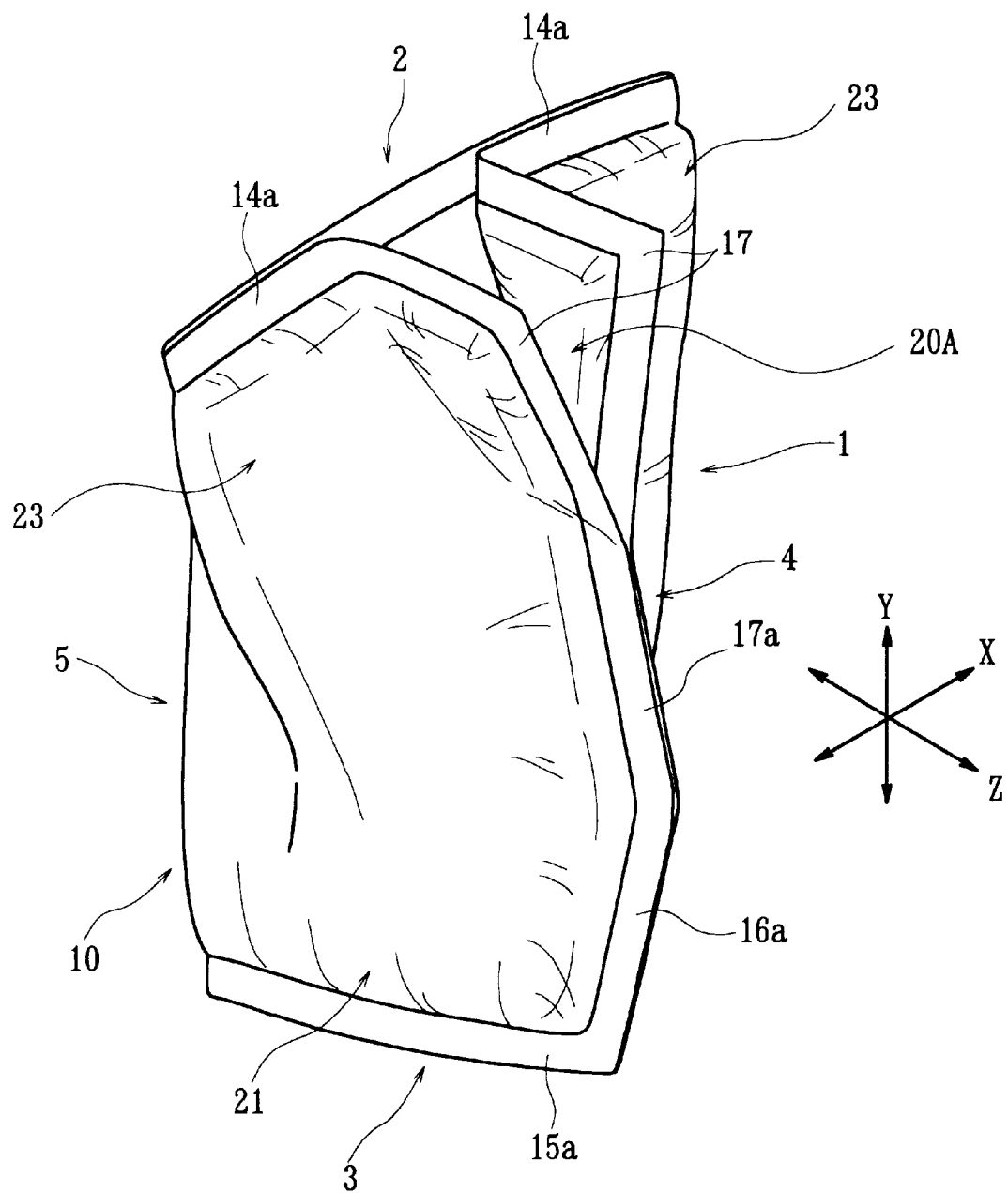
FIG. 10 shows a modification of the urine absorbing pad of FIG. 1.
Figure 11:
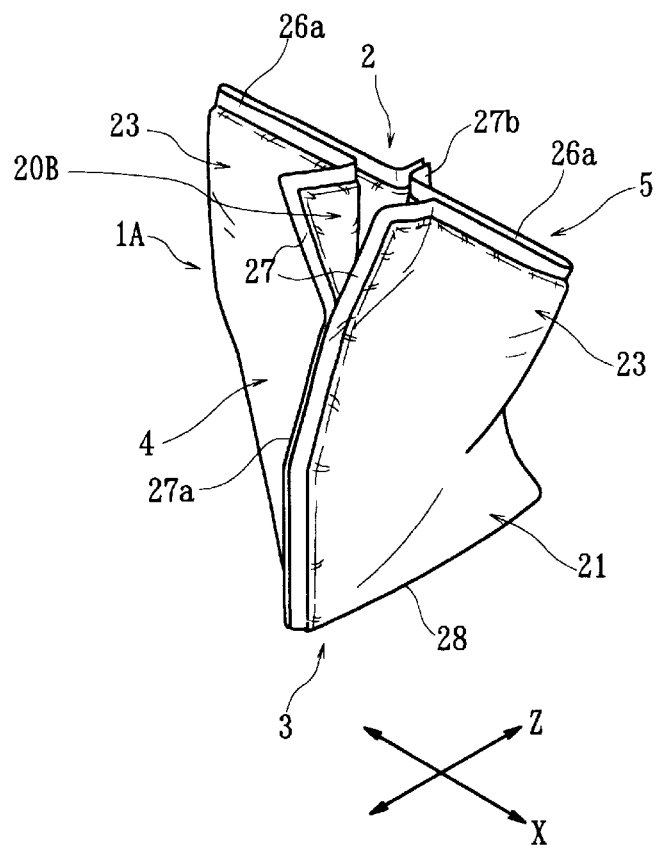
FIG. 11 shows a modification of the urine absorbing bad of FIG. 9(B)

On the other hand, the shape of the opening should not be limited to the slit shape but can be exemplified by ones shown in FIGS. 10 and 11. FIG. 10 shows a modification of the urine absorbing pad shown in FIG. 1, in which an opening 20A is formed between the upper end 2 and the edge portions 17 and 17. FIG. 11 shows a modification of the urine absorbing pad shown in FIG. 9(B), in which an opening 20B is formed between the upper end 2 and the opposed faces of the edge portion 27. Here in the modification shown in FIG. 10, the bag body 1 is formed by setting the folding lines Ly1 and Ly1 at a distance of more than one quarter of the transverse size of the developed laminate 10 from the transverse ends of the upper end edge portion 14.

The developed shape of the laminate 10 should not be limited to that shown in FIG. 8. For example, the edge portions 16 need not be sloped straight but may also be curved. Alternatively, the sloped edge portions 16 need not be formed, but the laminate 10 may also be formed into a rectangular shape. However, if the laminate 10 is in a rectangular shape, the wearing side 4 at the lower end 3 will protrude at an acute angle toward the wearer. Therefore, it is preferable to form the sloped edge portions 16.

Figure 12:
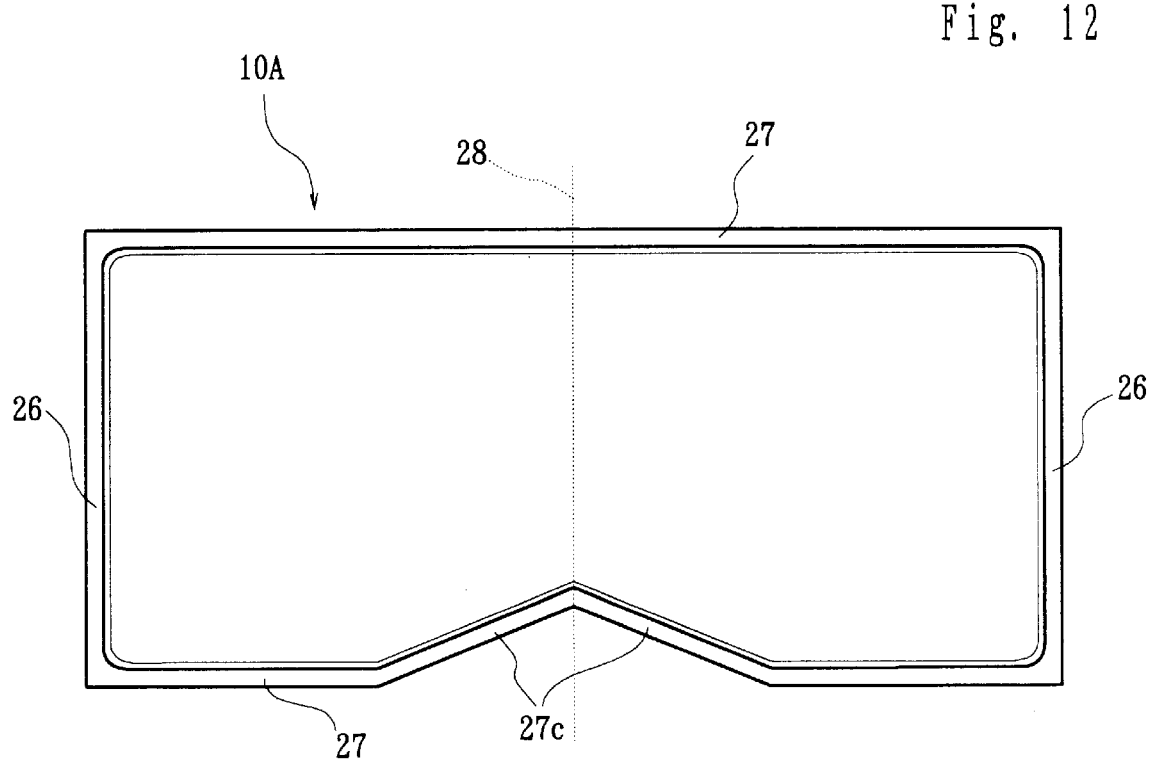
FIG. 12 is a developed top plan view of a laminate forming the bag body of the urine absorbing pad of FIG. 11.

Incidentally, the second embodiment shown in FIG. 9(B) has been described by adopting the rectangular shape for the developed laminate 1A. In this case, the wearing side 4 at the lower end 3 will sharply protrude toward the wearer, as shown in FIG. 9(B). This protrusion is similar to that of the above-described case in which the laminate 10 is in a rectangular shape. Therefore, as shown in FIG. 12, one of the edge portions 27 of the laminate 10A is preferably deformed to have sloped edge portions 27c which are symmetric with respect to the folding portion 28, thereby reducing the size of the laminate 10A at the folding portion 28. The urine absorbing pad shown in FIG. 11 is formed of the laminate 10A having the developed shape shown in FIG. 12.

The urine absorbing pad thus constructed can also be employed for infants or male children. Furthermore, the urine absorbing pad may be used for the urinary organ of a female adult by making the opening wider in the transverse direction (or in the direction X) and by providing means for preventing the urinary leakage and adhering to her body.

As has been described hereinbefore, the urine absorbing pad of the invention can be stably worn on the human body. Further, the urine absorbing pad can be reliably fitted on the urinary organ so that urine leakage is minimized or prevented. Moreover, the urine absorbing pad can absorb and reserve more urine as a whole.

In the foregoing specification, the invention has been described in relation to preferred embodiments and many details have been set forth for the purpose of illustration. It will be apparent to those skilled in the art that the invention is susceptible to additional embodiments and that certain of the details described herein can be varied considerably without departing from the basic principles of the invention.

Further, 'comprises/comprising' when used in this specification is taken to specify the presence of stated features, integers, steps or components but does not preclude the presence or addition of one or more other features, integers, steps, components or groups thereof.

What is claimed is:

1. A urine absorbing pad comprising a laminate including: a liquid permeable internal surface sheet; a liquid impermeable external surface sheet; and an absorbent core sandwiched between the internal and external surface sheets, the laminate being folded with its internal surface sheet directed inward to form a bag body which is closed but for an opening, wherein the bag body is a generally tetra-pack shape including: a wearing side portion for facing the wearer; a back side portion opposite to the wearing side portion; and two lateral side portions between the wearing side portion and back side portion, the wearing side portion and back side portion being continued at an upper end of the bag body, the two lateral side portions being continued at a lower end of the bag body, the upper end and the lower end being completely closed and extended substantially at a right angle with respect to each other, the spacing between the wearing side portion and back side portion being larger as extending toward the lower end, the opening being positioned in the wearing side portion and closer to the upper end than the lower end, and the opening being formed into a slit shape extending from the upper end to the lower end.

2. The urine absorbing pad according to claim 1, wherein in a developed state, the laminate is substantially symmetric with respect to a center line and contoured to have upper and lower edge portions opposed to each other and two side edge portions substantially symmetric with respect to the center line, and wherein the bag body is formed such that: two side portions of the upper edge portion are folded along folding lines, which are substantially symmetric with respect to the center line, toward a center portion of the upper edge portion and are adhered to the center portion of the upper edge portion thereby to form the upper end; the lower edge portion is folded along the center line into two and the two folded portions of the lower edge portion are adhered to each other thereby to form the lower end; and the two side edge portions confront each other and are adhered to each other except for portions for forming the opening.

3. The urine absorbing pad according to claim 2, wherein the side edge portions have slopes so that the tetra-pack shape of the bag body is deformed to eliminate the acute peak protruding toward the wearer on the lower end.

4. The urine absorbing pad according to claim 3, wherein a pair of elastic members for clamping a penis therebetween in use are provided on the opening-forming portions of the side edge portions of the laminate.

5. The urine absorbing pad according to claim 4, wherein the confronting faces of the elastic members are formed with grooves and ridges.

6. The urine absorbing pad according to claim 5, wherein a urine guide layer, as extended from a position to confront the opening to the lower end, is provided on the internal surface sheet.

7. The urine absorbing pad according to claim 1, wherein in a developed state, the laminate is substantially symmetric with respect to a center line and contoured to have upper and lower edge portions opposed to each other and two side edge portions substantially symmetric with respect to the center line, and wherein the bag body is formed such that: the upper edge portion and the lower edge portion are individually folded along the center line into two and the two folded portions of the upper and lower edge portions are individually adhered to each other except for portions for forming the opening; and the side edge portions are individually folded into two and the two folded portions of the side edge portions are individually adhered to each other, so that the center line forms the lower end and the side edge portions form the upper end.

8. The urine absorbing pad according to claim 7, wherein the lower edge portion has slopes substantially symmetric with respect to the center line so that the tetra-pack shape of the bag body is deformed to eliminate the acute peak protruding toward the wearer on the lower end.

9. The urine absorbing pad according to claim 8, wherein a pair of elastic members for clamping a penis therebetween in use are provided on the opening-forming portions of the side edge portions of the laminate.

10. The urine absorbing pad according to claim 9, wherein the confronting faces of the elastic members are formed with grooves and ridges.

11. A urine absorbing pad comprising a laminate including: a liquid permeable internal surface sheet; a liquid impermeable external surface sheet; and an absorbent core sandwiched between the internal and external surface sheets, the laminate being folded with its internal surface sheet directed inward to form a bag body which is closed but for an opening, wherein the bag body is of a generally tetra-pack shape including: a wearing side portion for facing the wearer; a back side portion opposite to the wearing side portion; and two lateral side portions between the wearing side portion and back side portion, the wearing side portion and back side portion being continued at an upper end of the bag body, the two lateral side portions being continued at a lower end of the bag body, the upper end and the lower end being extended substantially at a right angle with respect to each other, the lower end being completely closed and the upper end being partially closed, the spacing between the wearing side portion and back side portion being larger as extending toward the lower end, the opening being formed into a generally triangular shape, of which: one side is defined by the non-closed portion of the upper end; and the remaining two sides have flaps extending therefrom toward the wearer.

12. The urine absorbing pad according to claim 11, wherein in a developed state, the laminate is substantially symmetric with respect to a center line and contoured to have upper and lower edge portions opposed to each other and two side edge portions substantially symmetric with respect to the center line, and wherein the bag body is formed such that: two side portions of the upper edge portion are folded along folding lines, which are substantially symmetric with respect to the center line, toward a center portion of the upper edge portion and are adhered to the center portion of the upper edge portion except for portions for forming the one side of the triangular opening thereby to form the upper end; the lower edge portion is folded along the center line into two and two folded portions of the lower edge portion are adhered to each other thereby to form the lower end; and the two side edge portions confront each other and are adhered to each other except for portions for forming the two sides of the triangular opening.

13. The urine absorbing pad according to claim 12, wherein the side edge portions have slopes so that the tetra-pack shape of the bag body is deformed to eliminate the acute peak protruding toward the wearer on the lower end.

14. The urine absorbing pad according to claim 13, wherein a urine guide layer, as extended from a position to confront the opening to the lower end, is provided on the internal surface sheet.

15. The urine absorbing pad according to claim 11, wherein in a developed state, the laminate is substantially symmetric with respect to a center line and contoured to have upper and lower edge portions opposed to each other and two side edge portions substantially symmetric with respect to the center line, and wherein the bag body is formed such that: the upper edge portion and the lower edge portion are individually folded along the center line into two and the two folded portions of the upper and lower edge portions are individually adhered to each other except portions for forming the two sides of the triangular opening; and the side edge portions are individually folded into two and the two folded portions of the side edge portions are individually adhered to each other except for portions for forming the one side of the triangular opening, so that the center line forms the lower end and the side edge portions form the upper end.

16. The urine absorbing pad according to claim 15, wherein the lower edge portion has slopes substantially symmetric with respect to the center line so that the tetra-pack shape of the bag body is deformed to eliminate the acute peak protruding toward the wearer on the lower end.

* * * * *